United States Patent [19]

Wunsch

[11] 4,117,117

[45] Sep. 26, 1978

[54] TRIDECAPETIDE HAVING GASTRIN EFFECT

[75] Inventor: Erich Wunsch, Tutzing, Germany

[73] Assignee: Max Planck-Gesellschaft zur Forderung der Wissenschaften, Gottingen, Germany

[21] Appl. No.: 808,517

[22] Filed: Jun. 21, 1977

[30] Foreign Application Priority Data

Jun. 23, 1976 [DE] Fed. Rep. of Germany ....... 2628006

[51] Int. Cl.$^2$ ..................... A61K 37/00; C07C 103/52
[52] U.S. Cl. ............................... 424/177; 260/112.5 R
[58] Field of Search .................. 260/112.5 R; 424/177

[56] References Cited

U.S. PATENT DOCUMENTS 3,931,141 1/1976 Wissman et al. .............. 260/112.5 R

FOREIGN PATENT DOCUMENTS 2,256,445 11/1972 Fed. Rep. of Germany .... 260/112.5 R

OTHER PUBLICATIONS

Chem. Abstract, 68 (1968), 8755oe.
Gregory et al., Gut 15, 683–685, (1974).
Chem. Abstract, 80 (1974), 146,514u.

*Primary Examiner*—Delbert R. Phillips
*Assistant Examiner*—Blondel Hazel
*Attorney, Agent, or Firm*—Fisher, Christen & Sabol

[57] ABSTRACT

The tridecapeptide having the general formula L-leucyl-L-glutamyl-L-glutamyl-L-glutamyl-L-glutamyl-L-glutamyl-L-alanyl-L-tyrosylglycyl-L-tryptophyl-L-leucyl-L-asparagyl-L-phenylalanineamide, or a salt or protected derivative thereof. Such tridecapeptide has gastrin activity. A process of preparation of such tridecapeptide, a process of use of it, and therapeutic or diagnostic agents incorporating it.

15 Claims, No Drawings

TRIDECAPEPTIDE HAVING GASTRIN EFFECT

BACKGROUND OF THIS INVENTION

1. Field of This Invention

This invention relates to a new tridecapeptide with the same effect as gastrin effect, and salts and protected derivatives of the new tridecapeptide, as well as a process for the production of the new tridecapeptide. Further, this invention relates to therapeutic and diagnostic agents which contain the new tridecapeptide and/or its salts.

2. Prior Art

Gastrin, which occurs in nature, causes a stimulation of the secretion activity of the stomach and of the pancreas. Gastrin can be used both as a therapeutic agent for the stimulation of the HCl secretion of the stomach and as a diagnostic agent for the determination of the HCl secretion capacity or for the immunological determination of the gastrin.

As is the case with all natural substances, the problem with gastrin consists in the fact that its isolation from, for example, animal organs is very time consuming and expensive, and succeeds only in achieving minimum yields. Also, the synthesis of gastrin (see Beacham, Nature 209, p 585, 1966) is relatively expensive because of the large number of amino acids which are contained in such peptide.

For this reason, attempts have been made to replace gastrin by some substance which is analogous to gastrin and which has fewer amino acids (pentapeptide, heptapeptide). However such peptides have the disadvantage that, in relation to gastrin, they have comparatively lower activity and are very quickly inactivated by the liver [see U. T. Strunz et al., Gastroenterology, 70, A-83/941, (1976)].

Gregory et al., Gut 15, 683-85 (1974), teaches the naturally occurring tridecapeptide minigastrin, which has a methionine radical in the 11-position.

BROAD DESCRIPTION OF THIS INVENTION

An object of this invention is to provide a new tridecapeptide having the gastrin effect, and salts and protected derivatives of such new tridecapeptide. Another object of this invention is to provide a process for the production of such new tridecapeptide. A further object of this invention is to provide therapeutic and diagnostic agents which contain such new tridecapeptide and/or salts thereof. A still further objects is to provide a process of using such therapeutic and diagnostic agents. Other objects and advantages of this invention are set forth herein or are obvious herefrom to one ordinarily skilled in the art.

The objects and advantages of this invention are achieved by the products, agents and methods of this invention.

The tridecapeptide of this invention differs from naturally-occurring tridecapeptide minigastrin [see Gregory et al, Gut, 15, 683-685, (1974)] by the fact that the methionine radical present in the 11-position in the case of the actual or naturally-occurring minigastrin is replaced by a leucine radical. The tridecapeptide of this invention, subsequently designated as 11-leucine-minigastrin, has, as compared to the natural minigastrin, the advantages of improved stability and of easier accessibility.

According to this invention, applicant succeeded in synthesizing a new polypeptide which only contains 13 amino acids, which has a satisfactory gastrin activity and which is only slowly inactivated by the liver.

The tridecapeptide of this invention, just like naturally-occurring gastrin, causes stimulation of the secretion activity of the stomach and of the pancreas. It may be used, just like gastrin, both as a theerapeutic agent for the stimulation of the HCl secretion of the stomach and as a diagnostic agent for the determination of the HCl secretion capacity or for the immunological determination of gastrin.

This invention involves a tridecapeptide of the formula L-leucyl-L-glutamyl-L-glutamyl-L-glutamyl-L-glutamyl-L-ananyl-L-tyrosyl-glycyl-L-tryptophyl-L-leucyl-L-asparagyl-L-phenylalanin amide, as well as the salts and protected derivatives of such tridecapeptide.

The tridecapeptide of this invention differs from the naturally-occurring tridecapeptide minigastrin described by Gregory et al., Gut, 15, 683-685 (1974), (besides gastrin), by the fact that the methionine radical present in the 11-position in the actual tridecapeptide is replaced by a leucine radical. The tridecapeptide of this invention, subsequently designated herein as 11-leucine-minigastrin, when compared to the natural tridecapeptide minigastrin, has the advantages of improved stability and of easier accessibility.

As used herein, the expression "salt" or "salts" includes those which are usual in peptide chemistry such as salts with inorganic bases such as ammonia, sodium hydroxide, potassium hydroxide and the like or with organic bases such as dimethylamine and the like.

As used herein, the term "protected derivative" or "protected derivatives" encompasses the derivatives provided with protective groups customary in peptide chemistry.

Examples of amino protective groups are for example, those of the acyl type (such as, formyl, phthalyl, trifluoroacetyl, p-tosyl, aryl phosphoryl, alkyl phosphoryl, phenyl sulfonyl, benzyl sulfonyl, tritylsulfenyl, o-nitrophenylsulfenyl, γ-chlorobutyryl or o-nitrophenoxyacetyl), of the alkyl type (such as, trityl, benzyl or alkylidene) or of the urethane type [such as, carbobenzoxy, p-bromo, p-chloro or p-methoxycarbobenzoxy, tolyloxy, allyloxy, cyclopentyloxy, cyclohexyloxy, t-butloxy or 1,1-dimethylpropyloxy-,2-(p-biphenyl)-2-propyloxy-carbonyl or benzylthiocarbonyl or 1-adamantyloxycarbonyl].

Examples of amide protective groups are xanthenyl, 2,4-dimethoxybenzyl, 2,4,6-trimethoxybenzyl and 4,4'-dimethoxybenzhydryl.

Examples of carboxyl protective groups are O-ester and S-ester (such as, methyl, ethyl, t-butyl, benzyl, cyanomethyl, phthalimidomethyl, 4-picolyl-, 2-p-tosyl ethyl, phenyl, p-nitrophenyl, thiophenyl or p-nitrobenzyl ester), amide or hydrazine (such as, trityl, phenyl, carbobenzoxy or t-butoxycarbonylhydrazide). Furthermore, the carboxyl group can be protected by the formation of salt.

Also, the radical of a polymer carrier is (considered as) a carboxyl or an amido protective group.

The production of the tridecapeptide of this invention, as well as the salts or protected derivatives thereof, can be accomplished in a manner customary in peptide chemistry.

Essentially, however, all methods of production are based on the successive condensation of amino acids or protected polypeptides — such condensation is carried out according to known methods.

The tridecapeptide of this invention may be produced by:
(a) condensing an amino acid or a peptide with another amino acid or peptide, whereby the amino group and carboxyl groups which do not participate in the formation of the peptide bond are possibly blocked by a suitable protective group, so that the tridecapeptide with the desired sequence of amino acids is obtained; and
(b) possibly the protective groups present are split off; and/or
(c) if desired, the tridecapeptide obtained is converted into salt.

For example, the condensation between the free amino group of a molecule and the free carboxyl group of another molecule can be carried out directly in the presence of a suitable condensation agent, for example, a carbodiimide such as dicyclohexylcarbodiimide or 1-cyclo-hexyl-3-morpholinyl-carbodiimide, and other condensation agents known in the literature. Preferably, the condensation takes place in the presence of dicyclohexylcarbodiimide with the addition of a 1,2-dinuclephile, such as N-hydroxybenzotriazol or N-hydroxysuccinimide, suppressing the racemization.

Furthermore, the condensation can also take place via suitable activated acyl derivative, such as, a mixed anhydride, an azide, p-nitrophenyl ester, 2,4,5-trichlorophenyl ester or N-nydroxysuccinimidyl ester.

Effectively, the conversion (condensation) takes place in an inert organic solvent, preferably in a polar organic solvent, for example, dimethyl formamide, dimethyl sulfoxide, acetonitrile or a halogenated hydrocarbon, such as, dichloromethane or chloroform. The conversion (condensation) can also effectively take place or occur at a temperature below ambient temperature.

The protective groups can be removed by means of known reactions, such as, by reduction with sodium in liquid ammonia, hydrogenation (for example, in the presence of a palladiium/activated charcoal catalyst), treatment with hydrogen halides, such as, hydrogen bromide or hydrogen chloride, in acetic acid, or treatment with trifluoroacetic acid, trifluoromethylsulfo acid or boric acid-trifluoroacetic acid-tris-anhydride, sometimes with the addition of scavengers, such as, anisol and thiolene.

For the production of the free amines from their salts, for example, after treatment with hydrogen halide in actic acid, the hydrobromide salt, for example is treated either with an ion exchanger or neutralized with an inorganic or organic base, for example, a tert. amine, such as triethylamine.

The method of purification of the tridecapeptide obtained is not critical. Advantageously, however the purification is accomplished by chromatography, for example, on "Sephadex", or by countercurrent distribution.

Preferably, however, the tridecapeptide of this invention is produced as follows:
(a) tert-butyloxycarbonyl-L-leycyl-L-glutamyl-(γ-tert.-butyl ester)-L-glutamyl (γ-tert.-butyl ester)-L-glutamyl(γ-tert.-butyl ester)-L-glutamyl(γ-tert.-butyl ester)-L-glutamic acid(γtert.-butyl ester) is combined with L-alanyl-O-tert.-butyl-L-tyrosyl-glycyl-L-tryptophyl-L-leucyl-L-asparagyl (β-tert.-butyl ester)-L-phenyl-alaninamide;
(b) the existing protective groups are split off by treatment with trifluoro acetic acid; and
(c) this (b) is subsequently cleaned and the product obtained is converted into its ammonium salt.

As mentioned above, the 11-leucine-minigastrin of this invention can be used in vivo both for the stimulation as well as for the determination of the capacity of the stomach for HCl secretion according to the method disclosed by R. Ottenjann, Clinical Gastroenterology, Editor L. Demling, Thieme Verlag (1973). This application thus concerns an agent with gastrin effect containing 11-leucine-minigastrin and/or its pharmaceutically applicable salts as an effective component.

The dosage should be regulated according to individual needs and may vary between 5 ug to 500 ug, preferably 50 to 300 ug, per individual (single) dose given from once to several times a day.

11-Leucine-minigastrin, as well as its pharmaceutically usable salts, can be used as drugs or diagnostic agents in the form of preparations which are present in mixture with an organically or inorganically inert carrier material suitable for the enteric or parentereol application. Examples of such inert carriers materials are water, gelatin, gum arabic, lactose, starch, magnesium stearate, talcum, vegetable oils, polyalkylene glycol and vaseline. The preparations can be in solid form, such as tablets, sugar-coated tablets, suppositories or in liquid form, such as, solvents, suspensions, sirups or emulsions. The preparations can be sterilized and/or can contain auxiliary substances, such as, conservators, stabilizers, linking or emulsifying agents or salts for the change of the osmotic pressure or as buffer. The preferred forms of application are solutions (ampules), tablets, and intranasal spray solutions.

Furthermore, the 11-leucine-minigastrin of this invention has a strong immuneactivity and can be used in immunological methods for in vitro detection of gastrin and/or minigastrin in liquids.

DETAILED DESCRIPTION OF THIS INVENTION

As used herein, all parts, percentages and ratios are on a weight basis unless otherwise stated or otherwise obvious herefrom to one ordinarily skilled in the art.

The following examples are intended to explain this invention in more detail. In these examples, the following abbreviations and symbols customary in peptide chemistry are used: *Amino acid abbreviations,* formed of 3 letters, in the case of which one is dealing as a rule with the 3 initial letters; *Numerical data in parenthesis* represents the position within the polypeptide chain and which are given no further addition, unless the pertinent compound occurs once more in the form of a further derivative, which however are provided continuously with the addition *a, b, c,* etc., whenever one starts out from *a* and additional derivatives are produced:

L as the statement of configuration;
Z for the benzyloxycarbonyl radical [see for example Bermann et al., Berichte d. Dtsch. Chem. Ges., vol. 65, (1932), 1192 ff];
SU for the N-hydroxysuccinimide radical;
tBu for the ter.-butyl radical; and
BOC for the tert.-butyloxycarbonyl radical [for example McKay et al., J. Am. Chem Soc., vol. 79, (1957), p. 4686, and Anderson et al., J. Am. Chem. Soc., vol. 79, (1957), p. 6180].

EXAMPLE 1

Production of fragment I (partial sequence 1-6)

The experimental execution is as follows:

(a) Benzyloxycarbonyl-L-glutamyl (γ-tert.-butyl ester)-L-glutamic acid (γ-tert.-butyl ester)-methyl ester (5-6a).

71.0 gm. (280 m mole) of H-Glu(OtBu)-OMe × HCl and 39.2 ml (280 m mole) of triethyl amine are mixed in 1 liter of dioxane at 10° C. with 121.5 gm. (280 m mole) of Z-Glu(OtBu)-OSU. The reaction mixture is evaporated under vacuum after 12 hours of stirring. The remaining residue is distributed between acetic acid and water. The two phases are separated. The separated acetic acid phase is washed successively with 10 percent potassium hydrogen carbonate solution, 5 percent potassium hydrogen sulfate solution and water. After drying over sodium sulfate, the solvent is evaporated in the vacuum and the residue of acetic ester/diisopropyl ester is reprecipitated. The reprecipitated residue has a melting point of 48° to 50° C; and $[\alpha]_D^{20} = -18.1°$ or $[\alpha]_{546}^{20} = -21.5°$ ($c = 1$, in methanol).

(b) Benzyloxycarbonyl-L-glutamyl (γ-tert.-butyl ester)-L-glutamic acid (γ-tert.-butyl ester) (5-6b).

125 gm. (233 m mole) of Z-Glu(OtBu)-Glu(OtBu)-OMe (5-6a) in 750 ml of dioxane/water (9:1) are saponified titrimetically at 20° C. with 223 ml of sodium hydroxide solution, while stirring. After acidification of the solution with the equivalent quantity of 1N hydrochloric acid, the dioxane is largely evaporated in the vacuum. The residue obtained is absorbed in acetic ester. The organic phase is exhaustively extracted with diluted potassium hydrogen carbonate solution and finally, after acidification of the combined extracts, it is converted again into acetic ester. The organic phase is washed with water until free of acid, is dried over sodium sulfate and is then evaporated in the vacuum. The yield is 115.0 gm (94 percent of theoretical).

An analytical sample is precipitated from diethyl ester as dicyclohexylamine salt and is recrystallized from methanol/diethyl ester. The recrystallized material has a melting point 145° to 147° C,; and $[\alpha]_D^{20} = -2.2°$ or $[\alpha]_{546}^{20} = -2.6°$ ($c = 2$, in methanol). The yield is 88 percent of theoretical.

(c) L-glutamyl (γ-tert.-butyl ester)-L-glutamic acid (γ-tert.-butyl-ester) (5-6c)

115 gm (220 m mole) of Z-Glu(otBu)-Glu(OtBu)-OH(5-6b) in 2 liter of 95 percent methanol is hydrogenated in the presence of palladium. After the reaction is completed, the solution is filtered from the catalyst. The filtrate is evaporated to dryness under vacuum. The residue is recrystallized material from methanol/diethyl ether. The recrystallized has a melting point of 194° to 195° C; and $[\alpha]_D^{20} = +25.2°$ or $[\alpha]_{546}^{20} = +29.2°$ ($c = 1$, in methanol).

(d) Benzyloxycarbonyl-L-glutamyl(γ-tert.-butyl ester)-L-glutamyl-(γ-tert.-butyl ester)-L-glutamic acid (γ-tert-butyl ester) (4-6a)

28 ml (200 m mole) of triethylamine, 86.9 gm (200 m mole) of Z-Glu(OtBu)-OSU and subsequently 16.2 ml (200 m mole) of pyridine are added to 77.6 gm. (200 m mole) of H-Glu(OtBu)-Glu(OtBu)-OH (5-6c) in 1 liter of dimethylformamide at 0° C. The reaction mixture is stirred for 2 hours at 0° C. and subsequently for 12 hours at ambient temperature. The reaction mixture is then evaporated under vacuum. The solid residue is distributed between acetic ester and diluted potassium hydrogen sulfate solution. The two phases are separated. The separated acetic ester phase is washed in water until free of sulfate and is dried over sodium sulfate. The solution is dried under vacuum and the residue of acetic ester/diisopropylether is crystallized. The crystallized material has a melting point of 107° to 109° C.; and $[\alpha]_D^{20} = -8.5°$ or $[\alpha]_{546}^{20} = -9.7$ ($c = 1$, in dimethyl formamide). The yield is 129.gm (91 percent of theoretical).

(e) L-glutamyl(γ-tert.-butyl ester)-L-glutamyl(γ-tert.-butyl ester)-L-glutamic acid (γ-tert.-butyl ester) (4-6b).

120 gm (170 m mole) of Z-Glu(OtBu)-Glu(OtBu)-Glu(OtBu)-OH (4-6a) in 2 liters of 80 percent acetic acid are catalytically hydrogenated (as customary) in the presence of palladium. After the reaction is completed and filtration conducted, the filtrate is concentrated under vacuum. The product is precipitated with water, filtered off, washed with water and finally dried under vacuum at 40° C over KOH. The product has a melting point of 149° to 151° C.; and $[\alpha]_D^{20} = +9.3°$ or $[\alpha]_{546}^{20} = +11.6°$ ($c = 1$, in 80% acetic acid). The yield is 95.0 gm (98 percent of theoretical).

(f) Benzyloxycarbonyl-L-glutamyl(γ-tert.-butyl ester)-L-glutamyl (γ-tert.-butyl ester)-L-glutamyl (γ-tert.-butyl ester)-L-glutamic acid (γ-tert.-butyl ester) (3-6a).

90.0 gm (157 m mole) of H-Glu(OtBu)-Glu(OtBu)-Glu(OtBu)-OH (4-6b) in 1.5 liter of dimethylformamide are mixed successively, while stirring, with 22.0 ml (157 m mole) of thiethylamine, 68.2 gm (157 m mole) of Z-Glu(OtBu)-OSU and, after 2 hours of stirring at 0° C., with 12.7 ml of pyridine. After another 12 hours of reaction at ambient temperature, the solvent is largely evaporated away and the residue is distributed between acetic ester and diluted potassium hydrogen sulfate solution. The phases are separated. The separated organic phase is subsequently washed well with diluted potassium hydrogen carbonate, potassium hydrogen sulfate solution and water, and is finally dried over sodium sulfate. The solution is evaporated under vacuum and the residue is precipitated from acetic ester/diiosopropylester. The precipitated residue has a melting point of 128° to 130° C.; and $[\alpha]_D^{20} = 10.1°$ or $[\alpha]_{546}^{20} = -11.9°$ ($c + 1$, in dimethylformamide). The yield is 123.0 gm. (88 percent of theoretical).

(g) L-glutamyl(γ-tert.-butyl ester)-L-glutamyl(γ-tert.-butyl ester)-L-glutamyl (γ-tert.-butyl ester)-L-glutamic acid (γ-tert.-butyl ester) (3-6b)

110 gm. (123 m mole) of Z-Glu(OtBu)-Glu(OtBU)-Glu(OtBu)-OH (3-6a) in 5 liters of 95% methanol are hydrogenated in the presence of palladium as a catalyst. After the reaction is completed and filtration conducted, the filtrate is evaporated under vacuum. The residue is precipitated from methanol/acetic ester. The precipitated residue has a melting point of 175° to 177° C.; and $[\alpha]_D^{20} = -8.5°$ or $[\alpha]_{546}^{20} = -9.9°$ ($c = 1$, in dimethylformamide). The yield is 92.0 gm (98 percent of theoretical).

(h) Benzyloxycarbonyl-L-glutamyl(γ-tert.-butyl ester)-L-glutamyl (γ-tert.butyl-ester)-L-glutamyl(γ-tert.-butyl ester)-L-glutamyl(γ-tert.butyl ester)-L-glutamic acid (γ-tert.-butyl ester) (2-6a)

85.0 gm. (112 m mole) of H-Glu-(OtBu)-Glu(OtBu)-Glu(OtBu)-Glu(OtBu)-OH (3-6b) and 15.7 ml (112 m mole) of triethylamine in 3 liters of dimethylformamide are mixed, while stirring, at 0° C. with 48.7 gm of Z-Glu(OtBu)-OSU and, after 2 hours, with 9.1 ml of pyridine. The reaction mixture is stirred for 24 hours at 0° C. and 24 hours at ambient temperature. After distilling off the solvent under vacuum, the oily residue obtained is processed as described for (3-6a). The residue has a melting point of 169° to 171° C.; and $[\alpha]_D^{20} = -10.6°$ or $[\alpha]_{546}^{20} = -12.6°$ ($c = 1$, in dimethylformamide). The yield is 109.0 gm. (90 percent of theoretical).

(i) L-Glutamyl(γ-tert.-butyl ester)-L-glutamyl(γ-tert.-butyl ester)-L-glutamyl(γ-tert.-butyl ester)-L-glutamyl(γ-tert.-butyl ester)-L-glutamic acid (γ-tert.-butyl ester) (2-6b)

35.0 gm (32.5 m mole) of Z-Glu(OtBu)-Glu(OtBu)-Glu(OtBu)-Glu-(OtBu)-Glu(OtBu)-OH (2-6a) in 4 liters of 95 percent methanol are deacylated (as customary) in the presence of palladium as catalyst. After the reaction is completed the product (partially precipitated during hydrogenation) is dissolved by heating and the solution is filtered from the catalyst. The filtrate is brought to dryness under vacuum and the product is precipitated from ethanol acetic ester. The precipitated product has a melting point of 194° to 195° C.; and $[\alpha]_D^{20} = -7.2°$ or $[\alpha]_{546}^{20} = -8.20°$ ($c = 1$, in 80 percent acetic acid). The yield is 28.7 gm. (93.5 percent of theoretical).

(j) tert.-butyloxycarbonlyl-L-leucyl-L-glutamyl(γ-tert.-butyl ester)-L-glutamyl-(γ-tert.-butyl ester)-L-glutamyl(γ-tert.-butyl ester)-L-glutamyl(γ-tert.-butyl ester)-L-glutamic acid (γ-tert.-butyl ester)(1-6a).

2.83 gm (3.0 m mole) of H-Glu(OtBu)-Glu(OtBu)-Glu(OtBu)-Glu(OtBu)-Glu(OtBu)-OH (2-6b) in 100 ml of dimethylformamide are mixed with 0.42 ml (3.0 m mole) of triethylamine, 1.08 gm (3.3 m mole) of BOC-Leu-OSU and subsequently with triethyl amine and 0.24 ml (3.3 m mole) of pyridine. The reaction mixture is stirred for 12 hours at ambient temperature and finally it is processed as described for (3-6a). The material had a melting point of 225° to 227° C. (decomp.); and $[\alpha]_D^{20} = -23.4$ or $[\alpha]_{546}^{20} = -27.0°$ ($c = 1$, in methanol). The yield is 3.0 gm (86 percent of theoretical).

EXAMPLE 2

Production of the Fragment II (partial sequence 7-13)

(a) Benzyloxycarbonyl-L-alanyl-O-tert.-butyl-L-tyrosylglycyl-L-tryptophyl-L-leucyl-L-asparagyl(β-tert.-butyl ester)-L-phenylalanine amide (7-13a)

37.0 gm (55 m mole) of H-Trp-Leu-Asp(OtBu)-Phe-NH₂ × HCl (10-13b-hydrochloride) [produced in the customary manner from Z-Trp-Leu-Asp(OtBu)-Phe-NH₂ after hydrogenolytical decarbobenzoxylation and precipitation from methanol/ether; see E. Wunsch et al., Hoppe-Seyler's J. Physiol Chem. 353, 1246, (1972)] and 27.5 gm (55 m mole) of Z-Ala-Tyr(OtBu)-Gly-OH(7-9a) in 1 liter of dimethylformamide are mixed, after cooling to −10° C., in succession with 6.05 ml (55 m mole) of N-methylmorpholine, 6.9 gm (60 m mole) of N-hydroxysuccinimide and 12.4 gm (60 m mole) of dicyclohexylcarbodiimide. The reaction mixture is stirred for 12 hours at 0° C. and subsequently for an additional 36 hours at ambient temperature. After cooling, the mixture is filtered off from urea and the filtrate is evaporated under vacuum. The residue is suspended in 90 percent methanol. The suspension is stirred for 15 minutes at 60° C. The product is sucked off, and is washed well with warm methanol and finally with diethyl ether. The product has a melting point of 223° C. (decomp.); and $[\alpha]_D^{20} = -29.8°$ or $[\alpha]_{546}^{20} = -35.6°$ ($c = 1$, in dimethylformamide). The yield is 51.0 gm (83 percent of theoretical).

(b) L-Alanyl-O-tert.-butyl-L-tyrosyl-glycyl-L-tryptophyl-L-leucyl-L-asparagyl-(β-tert.-butyl ester)-L-phenylalanineamide (7-13b)

23.0 gm (20.6 m mole) of Z-Ala-Tyr(tBu)-Gly-Trp-Ley-Asp(OtBu)-Phe-NH₂ (7-13a) in 1 liter of dimethylformamide are hydrogenated (as customary) in the presence of palladium as a catalyst with simultaneous titration using 0.27 N methanolic hydrochloric acid at pH 5.0. After the reaction is completed and filtration done, the filtrate is evaporated under vacuum and the solid residue is ground with diethyl ester. The product is filtered off, dried under vacuum over KOH, subsequently dissolved in 250 ml of dimethylformamide and mixed with 2.9 ml (20.6 m mole) of triethylamine and 1 liter of water. The precipitate formed thereby is sucked off, washed well with water and diethyl ether and finally dried under vacuum. The precipitate has a melting point of 203° to 204° C.; and $[\alpha]_D^{20} = -21.0°$ or $[\alpha]_{546}^{20} = -25.1°$ ($c = 1$, in dimethylformamide). The yield is 19.8 gm (98 percent of theoretical).

EXAMPLE 3

Condensation of the fragments I and II Tert.-butyloxycarbonyl-L-leucyl-L-glutamyl(γ-tert.-butyl-ester)-L-glutamyl-(γ-tert.-butyl ester)-L-glutamyl(γ-tert.-butyl ester)-L-glutamyl(γ-tert.-butyl ester)-L-glutamyl(γ-tert.-butyl ester)-L-alanyl-O-tert.-butyl-L-tyrosyl-glycyl-L-tryptophyl-L-leucyl-L-asparagyl)β-tert.-butyl ester)-L-phenylalanine-amide (1-13a).

0.6 gm (0.61 mole) of H-Ala-Tyr(tBu)-Gly-Trp-Leu-Asp(OtBu)-Phe-NH₂ (7-13b) and 1.06 gm (0.92 m mole) of BOC-Leu-Glu(OtBu)-Glu-(OtBu)-Glu(OtBu)-Glu(OtBu)-Glu(OtBu)-OH (1-6a) in 10 ml of dimethylaceto amide and 3 ml of hexamethylphosphoric acid trisamide are mixed, after cooling to −10° C., in succession with 0.116 gm (1.01 m mole) of N-hydroxysuccinimide and 0.190 gm (0.92 m mole) of dicyclohexylcarbodiimide. The reaction mixture is stirred for 48 hours at 4° C. and subsequently for 48 hours at ambient temperature. Finally the reaction mixture is poured into 90 ml of methanol. The precipitate which forms is filtered off and suspended in 200 ml of methanol. The suspension is stirred for 5 minutes at 60° C. and for 1 hour at ambient temperature. The filtered product is washed with methanol and diethyl ether and dried under vacuum. The product has a melting point of 255° C.; and $[\alpha]_D^{20} = -13.5°$ or $[\alpha]_{546}^{20} = -16.2°$ ($c = 1$, in hexamethylphosphoric acid trisamide. The yield is 1.07 gm (83 percent of theoretical).

50 ml of trifluoroacetic acid and 5 ml of anisol are poured over 0.99 gm (0.466 m mole) of BOC-Leu-Glu(OtBu)-Glu(OtBu)-Glu(OtBu)-Glu(OtBu)-Glu(OtBu)-Ala-Tyr(tBu)Gly-Trp-Leu-Asp(OtBu)-Phe-NH$_2$ (1-13a) under an argon atmosphere. The mixture is left standing at ambient temperature for 90 minutes — during this time, solution occurs. Subsequently, much diethyl ether is poured over the reaction mixture. The precipitate formed thereby is filtered off, washed will with diethyl ether and dried under vacuum over KOH. L-leucyl-L-glutamyl-L-glutamyl-L-glutamyl-L-glutamyl-L-glutamyl-L-ananyl-L-tyrosyl-glycyl-L-tryptophyl-L-leucyl-L-asparagyl-L-phenylalanineamide (1-13b) is obtained in the form of a colorless, amorphous powder. The powder is absorbed in 0.5 N ammonium hydroxide solution and is lyophilized. The yield is 0.763 gm (96 percent of theoretical, calculated for 5 × ammonium salt).

EXAMPLE 4

Purification of 11-leucine-minigastrin (a) Ion exchanger chromatography on DEAE-Sephadex A-25

A chromatography column (28 cm in length and 3 cm in diameter), is filled with an ion exchanger. DEAE-Sephadex A-25 (acetate form) equilibrated as customary with starting (initiating) buffer (0.5 m ammonium acetate solution, pH 8.5). A solution of 720 mg of the raw 11-leucin-minigastrin (peptide content: 83.5 percent; determined by quantitative amino acid analysis) in 12 ml of 0.5 m of ammonia solution is applied to the column and is extracted with the starting buffer at a flow rate of 166 ml per hour. The eluate is collected in portion of 125 ml in the cells of a collector for fractions (Serva-Linear II), whereby the distribution of peptide is determined by continuous registration of the extinction of the solution at 278 nm (LKB-Uvicord III). By lyophilization three times (twice from 0.5 percent ammonia), 577 mg of prepurified 11-leucine-minigastrin are isolated from the fractions 48-82.

(b) Distribution chromatography on Sephadex G-25

System of Solvents:

To a mixture of 2 liters of specially purified [cf E. Wunsch et al., Hoppe Seyler's J. Physiol. Chem. 353, 1716-1720 (1972)] secondary butanol, 100 ml of absolute ethanol and 2 liters of 0.1 m ammonium acetate solution (produced from 0.1 m of acetic acid by the addition of ammonia, until a pH of 5.4 is reached), acetic acid is added until the lower phase has a pH value of 6.0 after shaking.

Execution of the separation:

200 gm of Sephadex G-25 (fine) swollen in the lower phase of the above two-phase system for several hours are placed into a column (143 cm in length and 3 cm in diameter). After equilibration with 160 ml of upper phase, a solution of 200 mg of prepurified (see under a) L-leucine-minigastrin in a mixture of 10 ml of upper phase and 0.5 ml of 3 percent ammonia is applied to the column (slight quantities of insoluble components are previously separated by centrifuging) and are then eluted with upper phase at a flow rate of 50 ml per hour. The extract is always collected in portions of 50 ml in the cells of a fraction collector (Serva-Linear II), whereby the peptide distribution is determined by continuous registration of the extinction of the solution of 254 nm (LKB-Uvicord I). After combining fractions 18-24, the solvents are evaporated under vacuum. The remaining residue is dissolved in 20 ml of 5 percent ammonia and the peptide material is isolated by lyophilization. After twice, repeating the freeze drying 110 mg of pure water containing 11-leucine-minigastrin (ammonium salt) is obtained from 5 percent ammonia (insoluble components are always separated previously by means of filtration by a G-4 frit).

EXAMPLE 5

Ampule solutions of the following composition are produced in the customary manner:

| (a) | 11-leucine-minigastrin (ammonium salt) |    | 0.10 mg |
|     | mannite                                |    | 0.1 gm  |
|     | water for injection purposes           | ad | 2.0 ml  |
| (b) | 11-leucine-minigastrin (ammonium salt) |    | 0.20 mg |
|     | mannite                                |    | 0.1 gm  |
|     | water for injection purposes           | ad | 2.0 ml  |

EXAMPLE 6

Active substance dry ampules are produced in the customary manner containing the lyophilizate from:

| 11-leucine-minigastrin (ammonium salt) |    | 0.22 mg |
|----------------------------------------|----|---------|
| D-mannite free of pyrogene             |    | 10 mg   |
| water for injection purposes           | ad | 1.0 ml  |

For the dissolution, solvent ampules with the following content are produced:

| D-mannite free of pyrogene   |    | 113 mg |
|------------------------------|----|--------|
| water for injection purposes | ad | 2.4 ml |

What is claimed is:

1. The tridecapeptide having the general formula L-leucyl-L-glutamyl-L-glutamyl-L-glutamyl-L-glutamyl-L-glutamyl-L-alanyl-L-tyrosyl-glycyl-L-tryptophyl-L-leucyl-L-asparagyl-L-phenylalanineamide, or a salt or protected derivative thereof.

2. The tridecapeptide of claim 1, in unprotected form.

3. The tridecapeptide of claim 1 which is a salt thereof.

4. The tridecapeptide salt of claim 3 which is an ammonium salt thereof.

5. The tridecapeptide of claim 1 which has amino protective groups or amide protective groups or carbonyl protective groups.

6. A composition containing L-leucyl-L-glutamyl-L-glutamyl-L-glutamyl-L-glutamyl-L-glutamyl-L-alanyl-L-tyrosylglycyl-L-tryptophyl-L-leucyl-L-asparagyl-L-phenylalanineamide and/or a pharmaceutically acceptable salt thereof.

7. Process wherein the composition of claim 6 is used to stimulate the HCl secretion of the stomach.

8. Process wherein the composition of claim 6 is used to determine the HCl secretion capacity of the stomach.

9. Process wherein L-leucyl-L-glutamyl-L-glutamyl-L-glutamyl-L-glutamyl-L-glutamyl-L-alanyl-L-tyrosyl-glycyl-L-tryptophyl-L-leucyl-L-asparagyl-L-phenylalanine-amide is used to make an immunological determination of gastrin or minigastrin.

10. The tridecapeptide of claim 3 which is a pharmaceutically acceptable salt thereof.

11. The tridecapeptide of claim 3 wherein said salt is with a base selected from the group consisting of ammonia, sodium hydroxide, potassium hydroxide and dimethylamine.

12. The tridecapeptide of claim 1 wherein said tridecapeptide has amino protective groups selected from the group consisting of formyl, phthalyl, trifluoroacetyl, p-tosyl, aryl phosphoryl, alkyl phosphoryl, phenyl sulfonyl, benzyl sulfonyl, tritysulfenyl, o-nitrophenylsulfenyl, γ-chlorobutyryl, o-nitrophenoxyacetyl, trityl, benzyl, alkylidene, carbobenzoxy, p-bromo, p-chloro or p-methoxycarbobenoxy, tolyloxy, allyloxy, cyclopentyloxy, cyclohexyloxy, t-butloxy, 1,1-dimethylpropyloxy,2-(p-biphenyl)-2-propyloxy-carbonyl, benzylthiocarbonyl and 1-adamantyloxycarbonyl.

13. The tridecapeptide of claim 1 wherein said tridecapeptide has amide protective groups selected from the group consisting of xanthenyl, 2,4-dimethoxybenzyl, 2,4,6-trimethoxybenzyl and 4,4'-dimethoxybenzhydryl.

14. The tridecapeptide of claim 1 wherein said tridecapeptide has carboxyl protective groups selected from the group consisting of methyl, ethyl, t-butyl, benzyl, cyanomethyl, phthalimidomethyl, 4-picolyl-, 2-p-tosyl ethyl, phenyl, p-nitrophenyl, thiophenyl or p-nitrobenzyl ester and trityl phenyl, carbobenzoxy or t-butoxycarbonylhydrazide.

15. A composition as claimed in claim 6 wherein said tridecapeptide is in mixture with an organically or inorganically inert carrier material suitable for the enteric or parentereol application.

* * * * *